US010799294B2

(12) United States Patent
Rotenberg et al.

(10) Patent No.: US 10,799,294 B2
(45) Date of Patent: Oct. 13, 2020

(54) VIRTUAL OPERATING ROOM LAYOUT PLANNING AND ANALYSIS TOOL

(71) Applicants: Michael Jonathan Rotenberg, Toronto (CA); Kelly Noel Dyer, Toronto (CA); Kirusha Srimohanarajah, Toronto (CA); SYNAPTIVE MEDICAL (BARBADOS) INC., Bridgetown (BB)

(72) Inventors: Michael Jonathan Rotenberg, Toronto (CA); Kelly Noel Dyer, Toronto (CA); Kirusha Srimohanarajah, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 16/308,994

(22) PCT Filed: Jun. 13, 2016

(86) PCT No.: PCT/CA2016/050674
§ 371 (c)(1),
(2) Date: Dec. 11, 2018

(87) PCT Pub. No.: WO2017/214696
PCT Pub. Date: Dec. 21, 2017

(65) Prior Publication Data
US 2019/0307510 A1    Oct. 10, 2019

(51) Int. Cl.
*G06T 17/00* (2006.01)
*G06T 19/20* (2011.01)
(Continued)

(52) U.S. Cl.
CPC .............. *A61B 34/10* (2016.02); *G06T 17/00* (2013.01); *G06T 19/20* (2013.01); *G16H 40/63* (2018.01);
(Continued)

(58) Field of Classification Search
None
See application file for complete search history.

(56) References Cited

U.S. PATENT DOCUMENTS

| 2009/0112538 | A1* | 4/2009 | Anderson | G06Q 10/06 |
| | | | | 703/6 |
| 2014/0276855 | A1* | 9/2014 | de la Barrera | A61B 34/20 |
| | | | | 606/87 |
| 2017/0189127 | A1* | 7/2017 | Weir | A61B 34/32 |

FOREIGN PATENT DOCUMENTS

WO        2014159350 A1    10/2014

OTHER PUBLICATIONS

PCT International Search Report and Written Opinion relating to PCT application No. PCT/CA2016/050506, dated Jun. 13, 2016.
(Continued)

*Primary Examiner* — Yanna Wu
(74) *Attorney, Agent, or Firm* — Rowand LLP

(57) ABSTRACT

A method and system to generate an operating room layout plan for a surgical procedure involving a patient and a trajectory of access. A patient model is positioned in a virtual coordinate space representing the operating room, and is rendered, along with the trajectory of access relative to the patient, on a display. The trajectory of access defines a zone of operation in the virtual coordinate space. The planning system receives selection of a navigation camera location in the virtual coordinate space; renders a navigation camera model visually indicating an operative field of view; determines whether the navigation camera has a direct line-of-sight to the zone of operation and, if not, indicates an error; and outputs the operating room layout plan based on the location of the models in the virtual coordinate space.

23 Claims, 10 Drawing Sheets

(51) Int. Cl.
*A61B 34/10* (2016.01)
*G16H 40/63* (2018.01)
(52) U.S. Cl.
CPC ... *A61B 2034/101* (2016.02); *A61B 2034/105* (2016.02); *A61B 2034/107* (2016.02); *G06T 2210/41* (2013.01); *G06T 2219/2004* (2013.01)

(56) References Cited

OTHER PUBLICATIONS

PCT International Preliminary Report of Patentability relating to PCT application No. PCT/CA2016/050506 dated Oct. 11, 2018.

* cited by examiner

VIRTUAL OPERATING ROOM LAYOUT PLANNING AND ANALYSIS TOOL

FIELD

The present application generally relates to image-guided medical procedures and navigation systems used to track objects in an image-guided medical procedure.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field. Optical tracking systems, used during a medical procedure, track the position of a part of the instrument that is within line-of-site of the optical tracking camera. These optical tracking systems also require a reference to the patient to know where the instrument is relative to the target (e.g., a tumour) of the medical procedure.

Three dimensional (3D) sensor systems are increasingly being used in a wide array of applications, including medical procedures. These sensor systems determine the shape and/or features of an object positioned in a scene of the sensor system's view. In recent years, many methods have been proposed for implementing 3D modeling systems that are capable of acquiring fast and accurate high resolution 3D images of objects for various applications.

In clinical procedures, three dimensional sensor systems may be used to track the location of instruments. Tracking of instruments relative to the patient and the associated imaging data is also often achieved by way of external hardware systems such as mechanical arms, or radiofrequency or optical tracking devices. As a set, these devices are commonly referred to as surgical navigation systems.

Pre-operative imaging data such as Magnetic Resonance Imaging (MRI), Computerized Tomography (CT) and Positron Emission Tomography (PET), is integrated into the surgical room statically through a viewing station, or dynamically through a navigation system. The navigation system registers devices to a patient, and a patient to the pre-operative scans, allowing for instruments to be viewed on a monitor in the context of the pre-operative information.

Port-based surgery is a minimally invasive surgical technique where a port is introduced to access a surgical region of interest using surgical tools. Unlike other minimally invasive techniques, such as laparoscopic techniques, a port diameter is larger than a tool diameter. Hence, the tissue region of interest is visible through the port, wherein exposed tissue in a region of interest, at a depth few centimetres below the skin surface, is accessible through a narrow corridor in the port.

The layout of an operating room for minimally invasive surgical operations can be a challenge. When a navigation system is being used, the layout cannot be arbitrarily changed without possibly impacting the correct registration of the patient and pre-operative scans and/or the ability to accurately track tools during the surgery. If the layout is unworkable or substandard, it may take significant time to correct and may require re-registration operations. Time in the operating room is typically costly and delays in initiating surgery may present complications for the patient and the staff, so rearranging equipment is to be avoided if at all possible.

BRIEF SUMMARY

The present application describes a method of generating an operating room layout plan for a surgical procedure involving a patient and a trajectory of access. The method includes defining a patient model in a virtual coordinate space representing the operating room, and rendering the patient model and the trajectory of access relative to the patient on a display based on selection of a patient position and the trajectory of access relative to the patient, the trajectory of access defining a zone of operation in the virtual coordinate space. The method further includes receiving selection of a navigation camera location in the virtual coordinate space; rendering a navigation camera model visually indicating an operative field of view; determining whether the navigation camera has a direct line-of-sight to the zone of operation and, if not, indicating an error; and outputting the operating room layout plan based on the location of the models in the virtual coordinate space.

In another aspect, the present application describes an operating room layout planning system for a surgical procedure involving a patient and a trajectory of access. The system includes a memory storing a plurality of models and a virtual coordinate space representing the operating room; a processor coupled to the memory; a display to render a view of the operating room defined in the virtual coordinate space; and a planning application containing instructions executable by the processor. When executed, the instructions may cause the processor to define a patient model in the virtual coordinate space and render the patient model and the trajectory of access relative to the patient on the display based on selection of a patient position and the trajectory of access relative to the patient, the trajectory of access defining a zone of operation in the virtual coordinate space. The instructions may further cause the processor to receive selection of a navigation camera location in the virtual coordinate space; render a navigation camera model visually indicating an operative field of view; determine whether the navigation camera has a direct line-of-sight to the zone of operation and, if not, indicating an error; and output the operating room layout plan based on the location of the models in the virtual coordinate space.

In yet a further aspect, the present application describes non-transitory computer-readable media storing computer-executable program instructions which, when executed, configured a processor to perform the described methods.

Other aspects and features of the present application will be understood by those of ordinary skill in the art from a review of the following description of examples in conjunction with the accompanying figures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the listed elements, without necessarily excluding any additional elements, and without necessarily requiring all of the elements.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
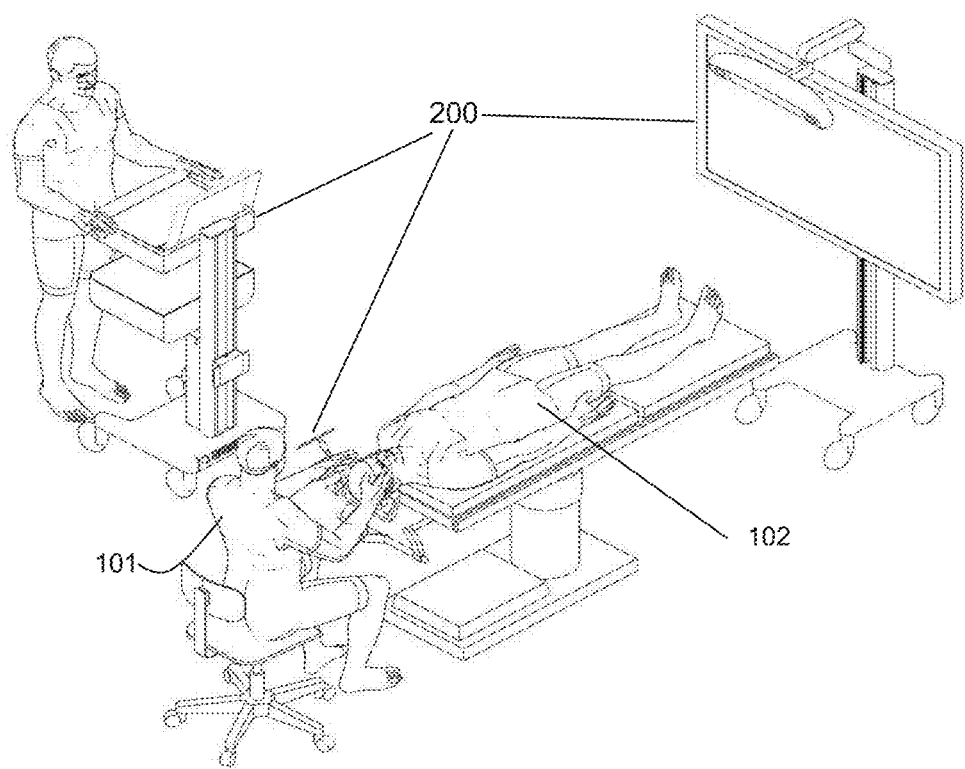
FIG. 1 diagrammatically illustrates, in perspective view, a navigation system.

Reference is first made to FIG. 1, which diagrammatically illustrates, in perspective view, a navigation system 200, such as a medical navigation system. The navigation system 200 is positioned in an operation room (OR) to be used to guide a surgeon in conducting a surgical procedure. In this example, the navigation system 200 supports, facilitates, and enhances minimally-invasive access port based surgery using a minimally-invasive access port-based surgical procedure. In this example, a surgeon 101 conducts a minimally-invasive access port based surgery on a subject, such as a patient 102, in an OR environment. The surgery may a neurosurgery, as in this example. In these circumstances, the surgeon 101 is positioned proximate the head of the patient 102. As will be discussed in greater detail below, the trajectory of access for the surgery may dictate the patient position for the surgery (which is supine in this example), so that the surgeon 101 can be in a comfortable position for the duration of the sometimes-lengthy surgery without suffering unnecessary fatigue. The trajectory of access, patient 102 position, and position of the surgeon 101 may impact the possible locations for the navigation system 200 and its various components. Laying out the OR with equipment located in suitable areas can be a significant factor in ensuring a smooth surgery.

In addition of the navigation system 200, the operating room may contain other equipment, such as surgical tool trays, carts, and booms. Some of this equipment may feature surgical lights, oxygen or other gas supplies, anesthesia supplies, etc., depending on the nature of the surgery being performed. In some cases, the layout of the OR must also account for the presence of nurses, an anesthesiologist, or other staff who may require a certain amount of space to monitor specific vitals or equipment, or to move between specific areas.

Figure 2:
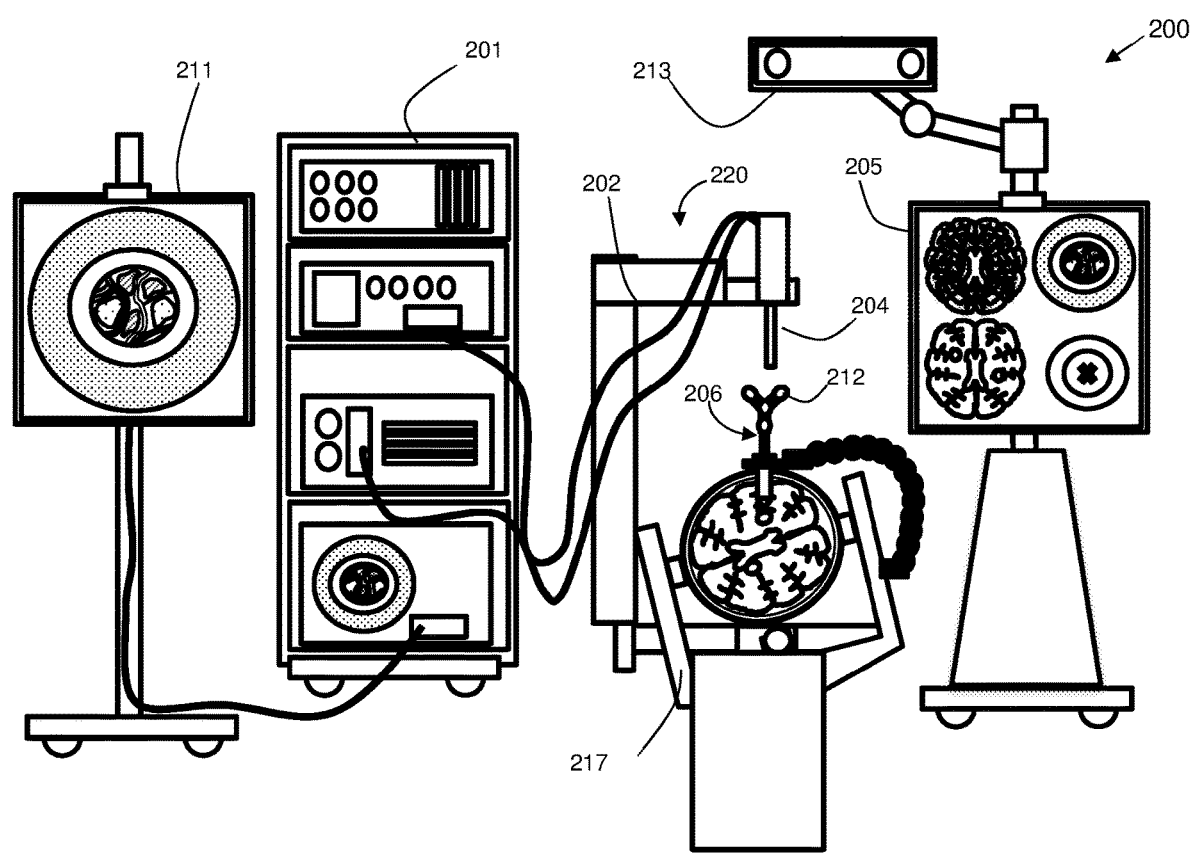
FIG. 2 diagrammatically illustrates an example of the navigation system.

Reference is now made to FIG. 2, which diagrammatically illustrates an example of the navigation system 200. The navigation system 200 may include an equipment tower 201, a tracking system 213, and at least one display device. e.g., a primary display device 211 and a secondary display device 205. The tracking system 213 may include optical imaging devices, e.g. cameras. In this example, the tracking system 213 includes two laterally spaced-apart cameras for stereoscopic vision. The camera may be a three-dimensional (3D) optical tracking stereo camera, such as a Northern Digital Imaging® (NDI) optical tracking stereo camera, by way of example. The navigation system 200 is to track at least one instrument, such as a surgical instrument, e.g., an access port 206, for assisting the surgeon 101 during the minimally-invasive access port-based surgical procedure.

The navigation system 200 may further include a device positioning unit, also referred to as a drive unit 220, having a robotic arm 202 that supports an optical device, such as an optical scope 204 or camera. The optical scope 204 may be positioned in line with the trajectory of access (co-axial with the access port 206) to enable the surgeon 101 (FIG. 1) to view down the access port 206. In the case where the optical scope 204 includes an image sensor, like a camera, the view may be displayed on one of the displays 205, 211 to assist the surgeon 101 in navigation. The view may also be integrated with other data, including pre-surgical plan information, pre-surgical imaging (like MRI, CAT scan, or ultrasound imaging, for example), and may be registered on the basis of registration of the patient in the OR space and registration of the surgical equipment relative to the patient, as tracked by the navigation system 200. The navigation system 200 may also track surgical instruments, like the access port 206 or other tools, in the OR space and may map models of those tools to a virtual space to which patient data has been mapped in order to render a combined display of the tools and the patient and/or pre-surgical imaging.

The equipment tower 201 may be mountable on a frame, e.g., a rack or a cart, and is configured to accommodate at least one of a computer operable by at least one a set of instructions, storable in relation to at least one non-transitory memory device, corresponding to at least one of planning software, navigation software, and robotic software, and a power supply, e.g., an AC adapter power supply.

In some example surgeries, a patient's head may be retained by a head holder 217, a craniotomy is performed, a dura flap is formed and retracted, and the access port 206 is inserted into the patient's brain. The tracking system 213 tracks and determines, e.g., in real-time by way of a set of instructions corresponding to tracking software and storable in relation to at least one non-transitory memory device, location data of at least one OR item, such as the robotic arm 202 and the at least one instrument, e.g., the access port 206. The tracked instrument may include at least one fiducial marker 212 mounted in fixed relation to the at least one OR item, e.g., the robotic arm 202 and the at least one instrument, e.g., the access port 206.

The secondary display device 205 may be configured to display real-time output from the navigation system 200. The displayed data may include at least one of an axial view, a sagittal view, at least one coronal view, and a view oriented relative to the at least one instrument, such as perpendicular to a tool tip, in-plane of a tool shaft, etc. The display may include multiple views.

The fiducial marker 212 may be a reflective sphere where the tracking system 213 is an optical tracking device. In some embodiments, the tracking system 213 may detect electromagnetic emissions and the fiducial marker 212 may be an electromagnetic marker. The three-dimensional position of the at least one fiducial marker 212 is determined by the tracking system 213 which is then able to map the location of the fiducial marker 212 to a virtual coordinate space and, thereby, position a model of the instrument to which the fiducial marker 212 is attached in the virtual coordinate space. The marker positions could be tracked relative to an object in the operating room such as the patient. Other types of markers that could be used would be RF, EM, LED (pulsed and un-pulsed), glass spheres, reflective stickers, or unique structures and patterns. The RF and EM may have specific signatures for the specific tools to which they are attached. The reflective stickers, structures, and patterns, glass spheres, LEDs may be detected using optical detectors, while RF and EM may be detected by using antennas.

Figure 3:
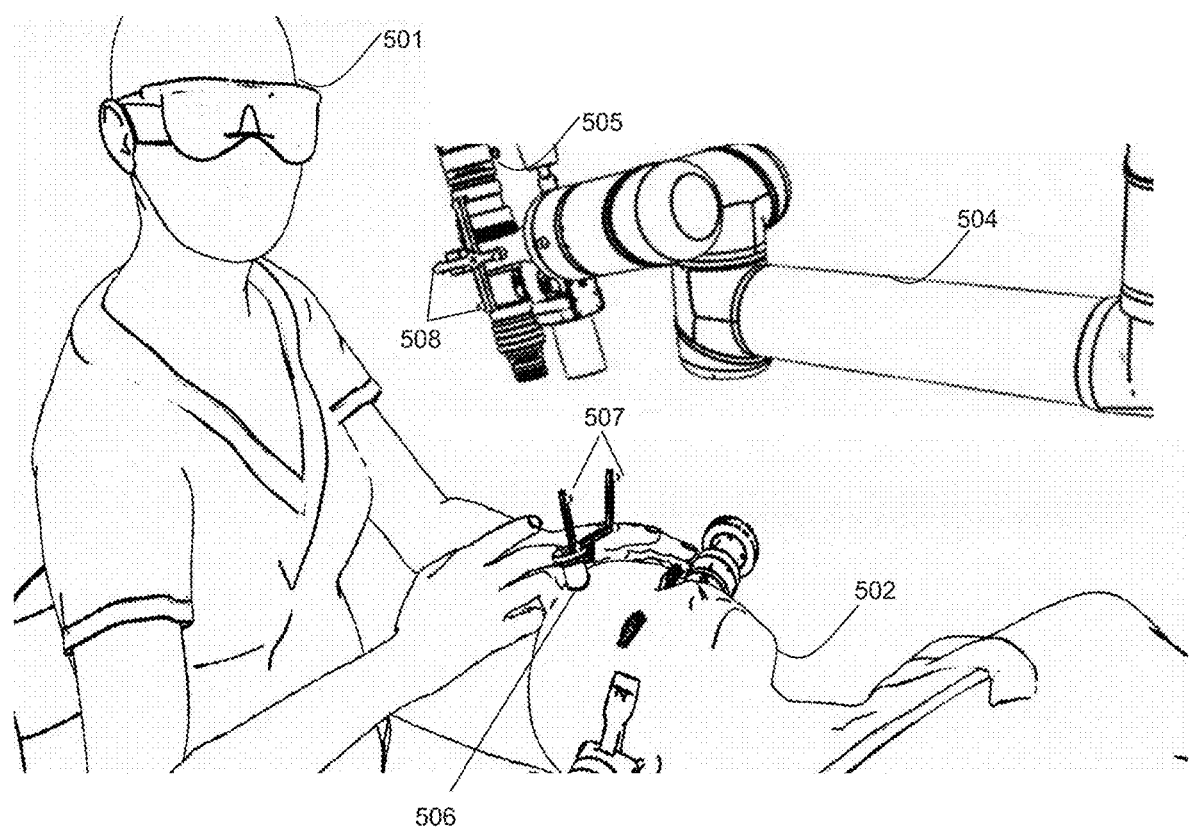
FIG. 3 shows a view of an example access port-based surgical procedure being conducted using the navigation system.

FIG. 3 shows a view of an example access port-based surgical procedure being conducted using the navigation system 200. In this example, a surgeon 501 is resecting a tumor from the brain of a patient 502 through an access port 506. An external scope 505 is coupled with a robotic arm 504, and is used to view down access port 506 at a sufficient magnification to allow for enhanced visibility down port 506. The output of external scope 505 is rendered on a visual display, such as a display device mounted perpendicular to the surgeon 501 for ease of viewing. Active or passive fiduciary markers, 507, 508, e.g., spherical markers, are disposed in a fixed geometrical arrangement in fixed relation to at least one of the access port 506 and the external scope 505 for facilitating their tracking (location of these tools) by the tracking system. The active or passive fiduciary markers, 507, 508, are sensed by sensors of the tracking system, whereby identifiable points are provided. A tracked instrument is typically identified by a sensing a grouping of active or passive fiduciary markers, 507, 508, whereby a rigid body, such as a tool, is identified by the tracking system, and whereby the position and pose in 3D of a tracked instrument, such as a tool, is determinable. Typically, a minimum of 3 active or passive fiduciary markers, 507, 508, are placed on a tracked tool to define the instrument. In many embodiments, four active or passive fiduciary markers, 507, 508, are used to track each tool.

As noted above, laying out the equipment in the OR is an important step to ensure a smooth and effective surgery. Operating room time is expensive and valuable and harm to the patient may result from delays. If a surgeon arrives to begin a surgery only to find that the operating room layout is substandard, or even impractical, then valuable time may be lost while equipment is rearranged, particularly where a navigation system is being used since the relative location of the camera, patient, trajectory of access, surgeon, etc., impact the ability of the navigation system to accurately and effectively track objects in the operating room space.

In one aspect, the present application describes a planning system and process for developing an operating room layout using a virtual coordinate space and models of equipment and personnel. The system and process start with the pre-operative surgical plan, which includes the trajectory of access. This plan restricts the possible patient positions. With a patient positioned defined, the surgeon's location may be selected based on the surgeon's preferred positioning in light of the trajectory of access and the patient position. Other equipment models may then be positioned in virtual coordinate space. For example, trays or other stationary devices may be assigned a location. A unit having a defined workable range of operation, like a drive unit with a robotic arm, may be positioned in the space. The model of the drive unit may include a visual indication of its operable range to enable it to be positioned in a location in which it can effectively reach the trajectory of access and/or any other area of the surgery to which it needs access. Visual indicators may assist users in positioning the drive unit such that its operable range includes the areas to which it needs to be able to reach.

In some embodiments, a navigation camera is to be positioned to assist in image-guided surgical operations. The navigation camera has a field of view within which it can effectively determine the position of trackable objects with sufficient accuracy. The system and process for developing an operating system layout may determine whether a navigation camera position results in the trajectory of access being positioned with the field of view to enable tracking of objects being used at the point of surgical operation.

The surgery, and the use of surgical instruments, may be expected to occur within a zone of operation proximate to and including the trajectory of access. The zone of operation may have any suitable geometric shape. The trajectory of access may be centered within the zone, in some cases. In some cases, the system and process may determine whether the full zone of operation is within the field of view and, moreover, whether the full zone of operation is within a line-of-sight of the navigation camera. In cases where the navigation camera includes two spaced-apart cameras, the system and process may determine whether the zone of operation is within a clear line-of-sight of each of the spaced-apart cameras.

The system and process may work with models in a three-dimensional virtual coordinate space. The virtual coordinate space models the operation room. In some cases, the operating room may be 3D-scanned to produce an accurate model of the room mapped to the virtual coordinate space. In some cases, the general dimensions of the room may be defined, including any doors, windows, etc. to model the space. In a simplified implementation, the walls and other physical features aside from the floor are not modeled in the virtual coordinate space, relying instead on the user to position items in close enough proximity to the operating table to avoid walls and other such physical restrictions.

The mapping and manipulation of three-dimensional models in a virtual coordinate space will be familiar to those persons of ordinary skill in the art. However, the process and system for laying out an operating room may introduce additional technical complications due to the interrelated nature of some of the equipment. Accordingly, the process and system may proactively test viability of layouts and provide warnings or other visual indications of problems with a selected layout due to conflicts between objects. For example, the process and system may regularly determine whether any objects interfere with the direct line-of-sight between the navigation camera and the zone of operation and/or the trajectory of access, so as to ensure no newly-placed objects impact the viability of the navigation system positioning.

The models in the three-dimensional coordinate space may be designed to be manipulated in a manner that replicates their mechanical properties in the real world. For example, the patient bed or stretcher may be linearly or vertically adjustable, or the bed portion of an MRI machine may have a linear range of motion, and those physical properties may be incorporated into the models so that the ranges of movement and resulting interaction with other modelled equipment may be observed.

The planning system may further apply rules during the planning process with respect to placement of respective models of equipment. For example, a rule may specify that, with the exception of the surgeon's chair, there must be 1-2 feet of clearance around the perimeter of the surgical table. In some embodiments, color coding or other visual or auditory signaling may be used to indicate to a user whether or not a particular piece of equipment is allowed to be in a particular place. For example, portions of the floor on which a particular piece of equipment are permitted may be colored green. The rules may be user configurable in some implementations.

An OR layout plan, once completed, may be stored for later access for the surgery, or for subsequent surgeries. In some embodiments, the OR layout plan may be output as a printed layout plan to guide staff in setting up the OR. In yet other embodiments, the OR layout plan may be rendered in an augmented reality (AR) or virtual reality (VR) system. Such an embodiment may permit a surgeon to view the OR layout from the perspective in which he or she will be situated to determine whether the OR layout is satisfactory of adjustments should be made. Once the OR layout is finalized, an AR system may be used to guide staff in placing real world equipment in the OR such that is properly aligned with the OR layout plan.

To illustrate the OR planning process and planning system, development of an example OR layout plan is now discussed.

Figure 4A:
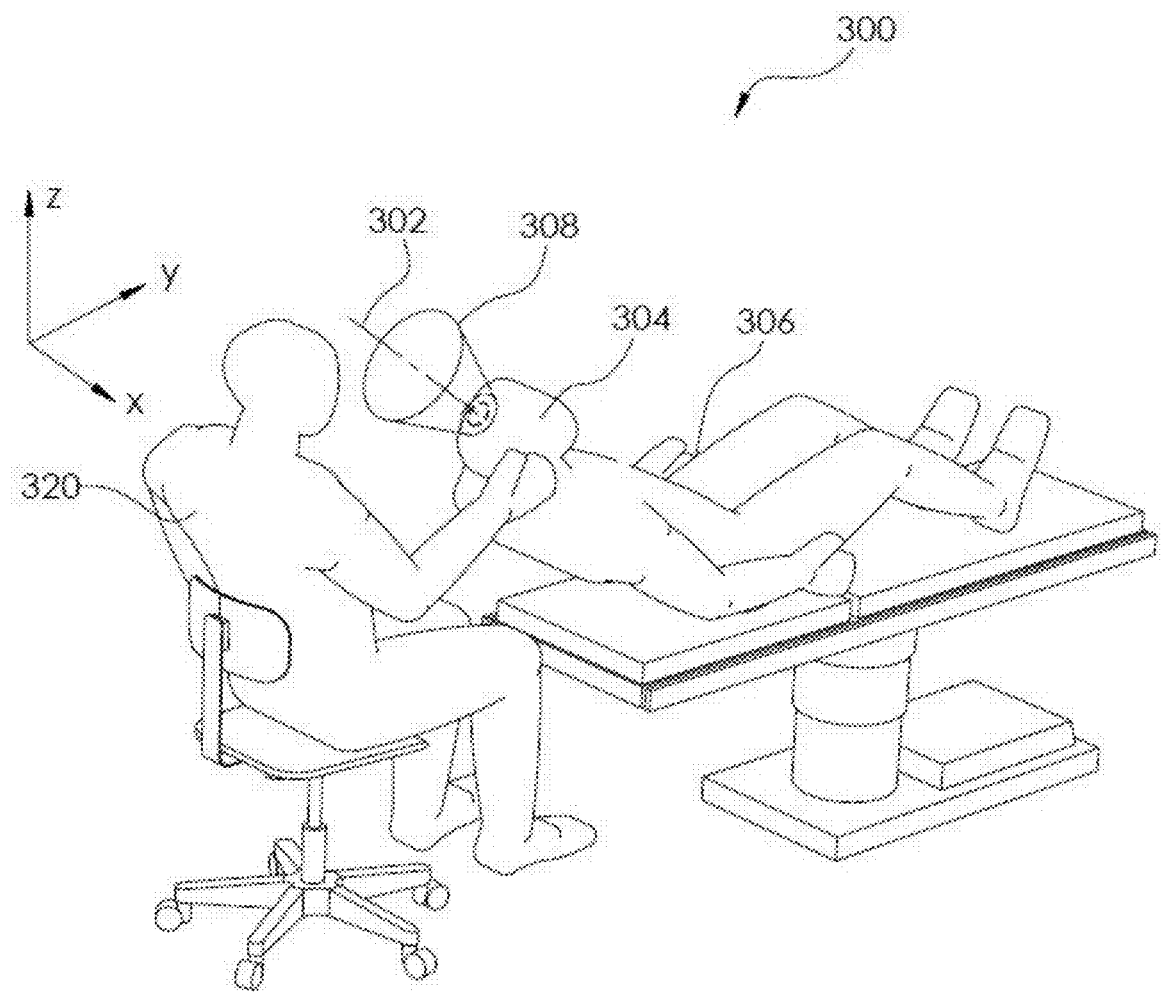
FIGS. 4A to 4E shows example views of a virtual coordinate space defined in memory of the planning system and containing models of equipment or personnel for a surgical procedure.

Reference will now be made to FIG. 4A, which shows, in perspective view, one example of a virtual coordinate space 300 defined in memory of the planning system. The pre-operative surgical plan defines a trajectory of access 302 vis-à-vis a patient. The trajectory of access 302 is at a particular location and three-dimensional angle with respect to a patient's skull 304. The location and angle at which the trajectory of access 302 is situated impacts the position into which the patient will need to be placed for the surgery, since the trajectory of access 302 needs to be at an accessible and comfortable position for the surgeon to operate. As examples, in some cases the patient may be prone (face-down), supine (face-up), or inclined (e.g. in a partly-reclined seated position). In the present example, a patient 306 is shown in a partly reclined position. Other positions may be more suitable depending on the preferences of the surgeon.

Having defined a patient position, a model of the patient is positioned in the virtual coordinate space 300. The planning system may obtain the trajectory of access 302 form a pre-operative surgical plan uploaded to (or otherwise input to) the planning system. The planning system may also obtain a patient position from the pre-operative surgical plan, or if not available it may provide a full or partial list of position options for selection. The planning system may restrict the available patient positions based on the nature of the facility (any restrictions inherent in the operating room table) and the trajectory of access 302 (e.g. eliminating those positions clearly inapplicable given the trajectory of access). Once patient position is fixed, the model of the patient is mapped to the suitable location in the virtual coordinate space 300. A projection of the patient and other objects (if any) in the operating room may be rendered on a two-dimensional display of the planning system.

Using user input devices, including keys, a touchscreen, a mouse, stylus, or other such instruments, a user of the planning system may alter the perspective from which the two-dimensional projected view is taken.

A model of a surgeon 320 may be rendered in the virtual coordinate space. Using user input devices, a user may be permitted to move the model of the surgeon 320 to position the surgeon in a location relative to the patient that will enable the surgeon 320 to access a zone of operation 308 easily. The model may be moved within an x-y plane parallel to the floor, and may be adjusted (within a range) in the z-direction to adjust seating height so as to position the surgeon a suitable height for the surgery. The model of the surgeon 320 may also be rotatable within the x-y plane to face the surgeon in the desired direction towards the trajectory of access 302.

The zone of operation 308 may be defined proximate the trajectory of access 302. In some embodiments, the trajectory of access 302 may define a centerline of the zone of operation 308. The zone of operation 308 is a three-dimensional volume proximate the trajectory of access 302 within which the tools of the operation will be used by the surgeon 320 and tracked by the navigation system during the surgery. In this example, the zone of operation 208 is shown as a frustoconical volume coaxial with the trajectory of access 302. The zone of operation 308 may be larger or smaller than the example shown, and may have other geometric shapes, including irregular shapes.

Figure 4B:
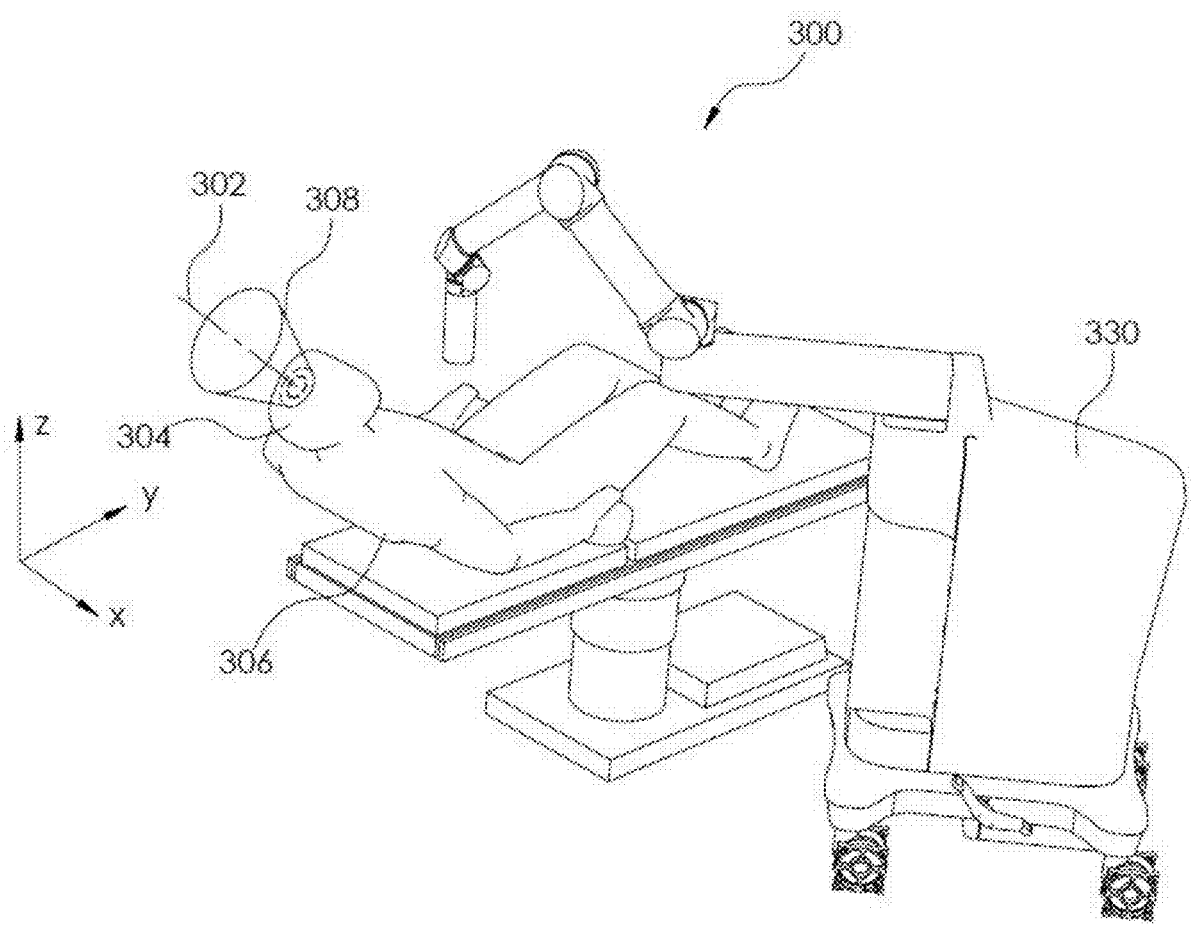

Reference is now made to FIG. 4B, which shows a perspective view of a further example of the virtual coordinate space 300. In this example, having positioned models of the patient 306 and the surgeon 320, new equipment for the operation may be added to the room. For example, the surgery may involve a drive unit having a robotic arm for holding surgical instruments and/or scopes/cameras. A model of the drive unit 330 may be positionable within the virtual coordinate space. Certain restrictions may be imposed by the planning system, such as a minimum distance between the drive unit 330 and the patient 306 and/or operating table (if the operating table is modeled) so as to ensure the drive unit 330 will not be located too close to the operating table.

Figure 4C:
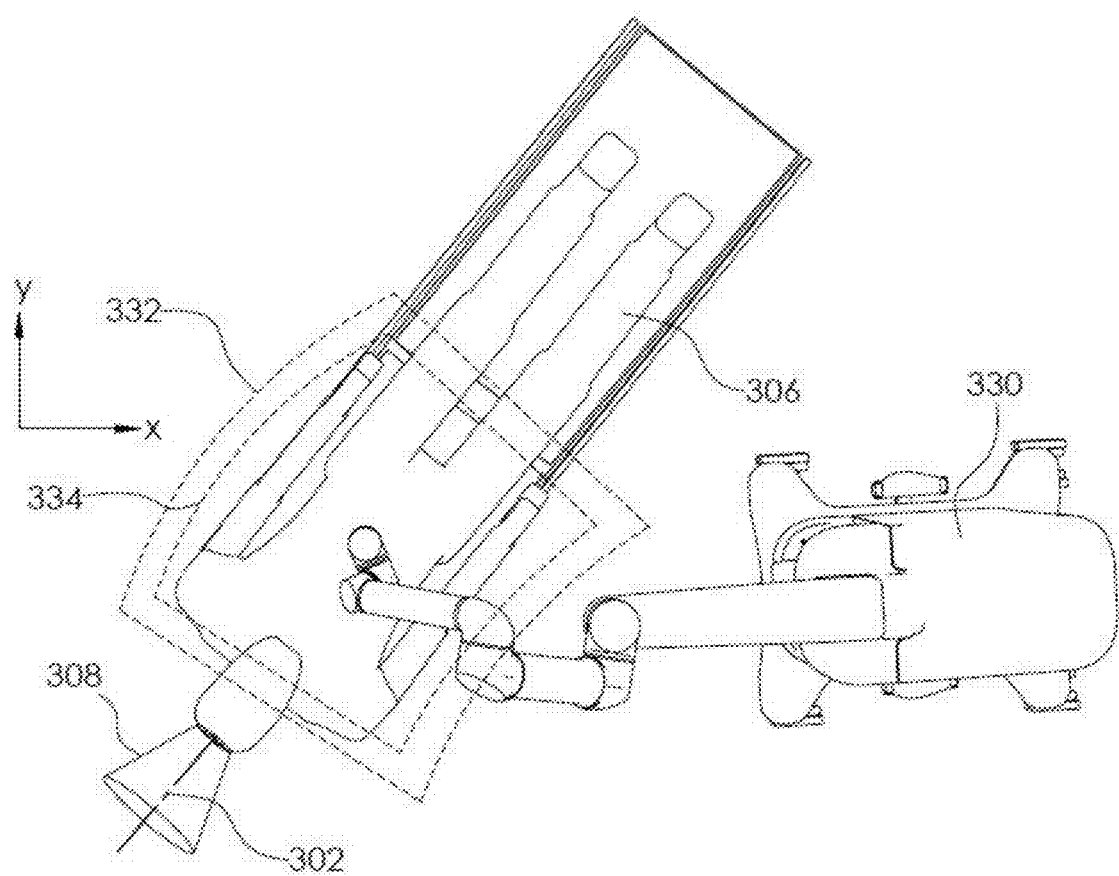

FIG. 4C shows the virtual coordinate space 300 in a plan view, i.e. from above, looking down onto the x-y plane. The planning system may assist in selecting a usable position for certain equipment, like the drive unit 330, by providing visual indications of operable ranges or positions. In this example, the planning system may visually indicate an operable range 332 for the robotic arm. The planning system may impose a rule or restriction that the operable range 332 include the trajectory of access 302 or at least some or all of the zone of operation 308 proximate the trajectory of access 302. The operable range 332 may include a maximum usable reach of the arm, and a minimum usable reach of the arm. This operable range 332 may be a three dimensional volume within which the trajectory of access 302 is to be located.

In the example shown, it will be noted that the operable range 332 does not include the trajectory of access 302 or any portion of the zone of operation 308. In some cases, this may mean that the drive unit 330 will be unable to properly position the robotic arm to assist with the surgery in this position. The planning system may indicate this as an error using visual or auditory alerts. For example, if the drive unit 330 is positioned as shown without the trajectory of access 302 and/or zone of operation 208 within the operable range 332, then an auditory message or tone may be output to indicate the error. In another example, a visual notification may be displayed to indicate the error. In one example, the operable range 332 visual displayed may change color when the drive unit 330 is positioned to include the trajectory of access 302. For instance, it may be colored red until it is positioned with the trajectory of access 302 in range, in which case the coloring of the operable range 332 is changed to green. The colors are examples only. Other conditions may be imposed in other circumstances; for example, if the robotic arm is to hold a camera above the access port, then it may be required that the operable range include some point along the trajectory of access 302, but not necessarily within the zone of operation 308. Other conditions may be suitable for other devices and surgeries.

In some instances the operable range 332 may be subdivided into usable and preferred volumes. For example within the operable range 332, a smaller sub-volume may be defined as an ideal range 334 or preferred range within which the trajectory of access 302 should be located.

Figure 4D:
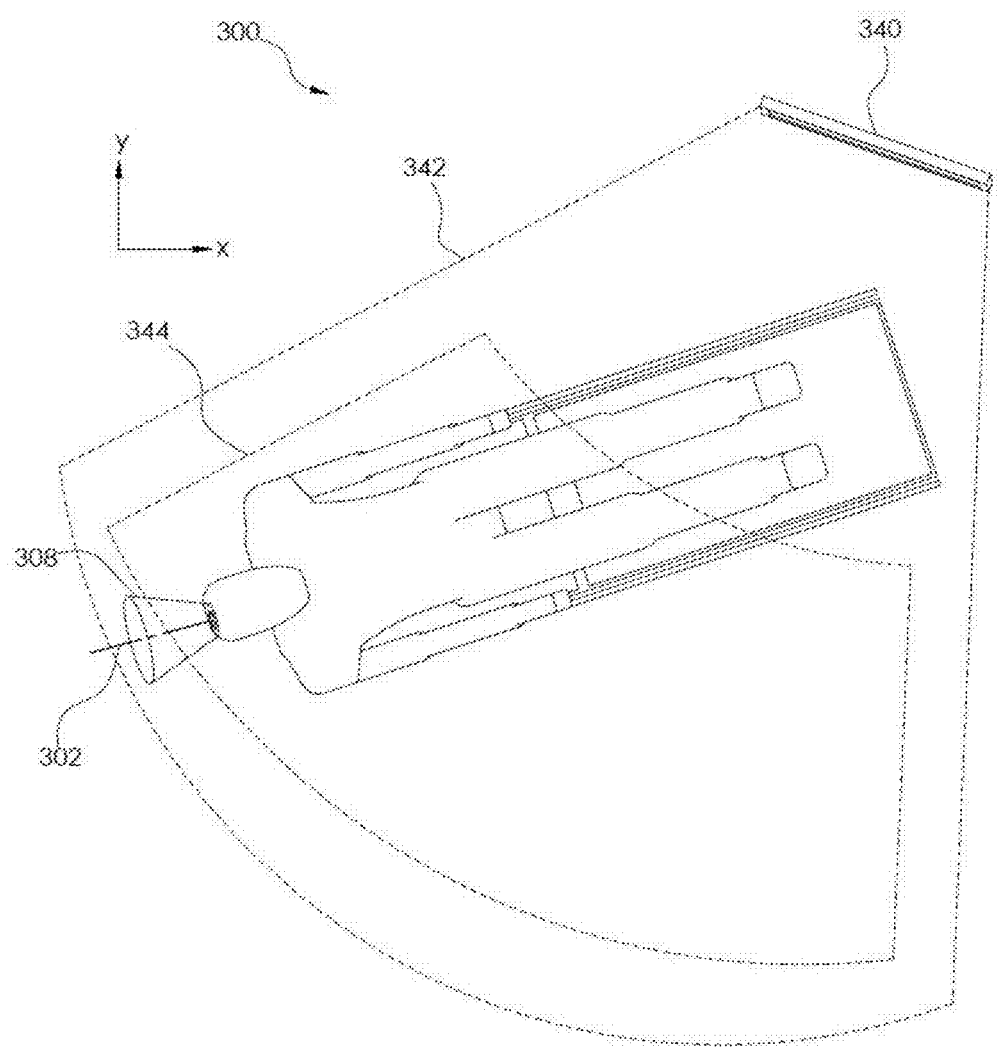

Reference is now made to FIG. 4D, which shows another plan view of the example virtual coordinate space 300. In this example, a model of the navigation camera 340 has been placed in the virtual coordinate space 300. The navigation camera 340 has a field of view 342. In some cases, within the field of view 342, a preferred field of view 344 may also be defined.

The navigation camera 340 is used to track instruments used during the surgery. Accordingly, it may be a requirement that the field of view 342 (or the preferred field of view 344) include the zone of operation 308 within which the tracked instruments will be used during surgery. As with the example drive unit mentioned above, the planning system may provide auditory or visual feedback to a user positioning the model to reinforce the objective of positioning the navigation system such that the field of view 342 includes the zone of operation 308.

Figure 4E:
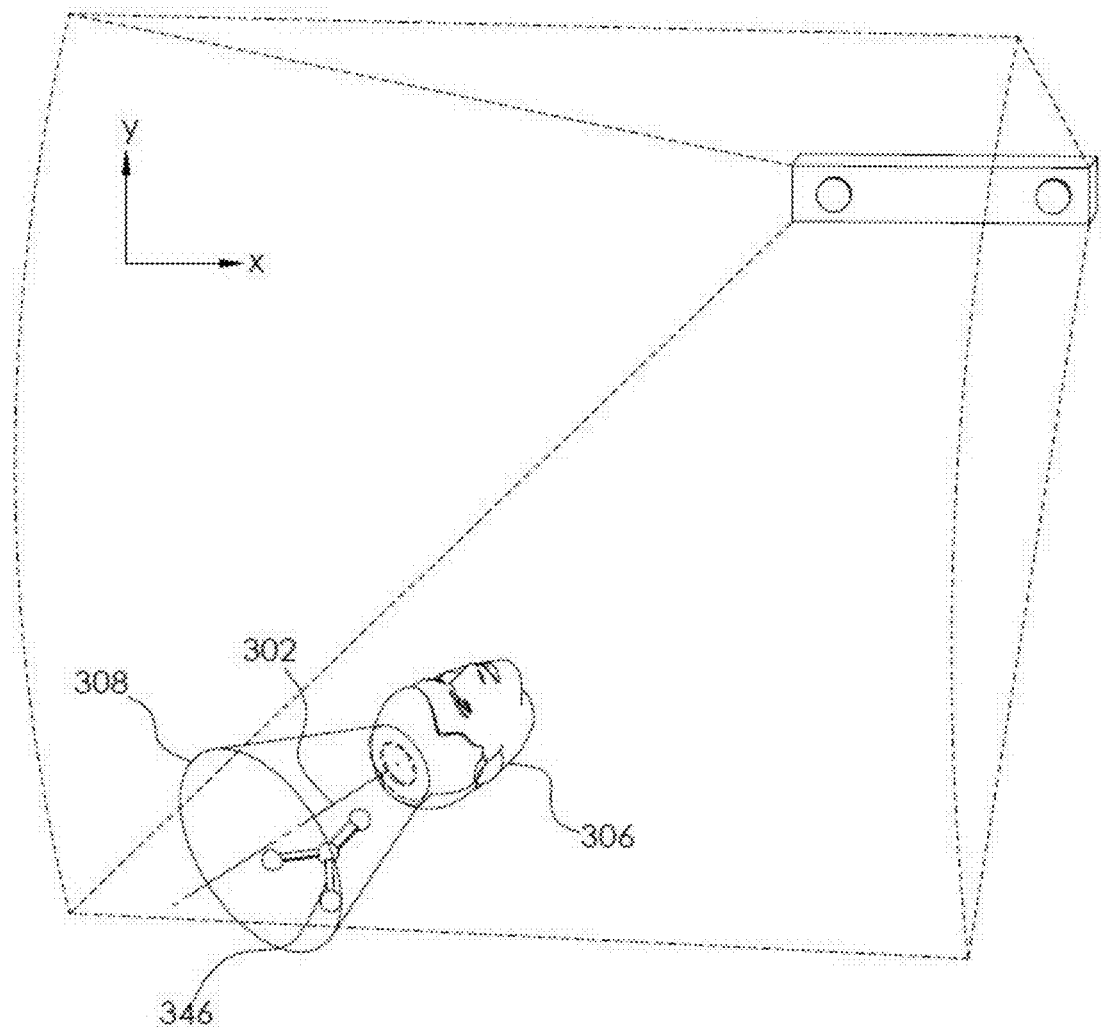

FIG. 4E shows a perspective view of a portion of the operating room layout, including the navigation camera 340, the head of the patient 306, and the zone of operation 308. A set of fiducial markers 346 in a fixed geometric pattern is shown within the zone of operation 308. This set of fiducial markers 346, in use, would be attached to a surgical instrument, such as an access port, a pointer device, or other such tools, for the purpose of determining the three-dimensional location of the tool during surgery so as to map a model of the tool to a virtual space containing pre-operative scan data regarding the patient, and correlated using patient registration. This enables the surgeon to see, on a display screen, the location of the tools relative to the patient and the MRI, CAT scan, ultrasound, or other scan data during the operation, thereby facilitating image-guided surgery.

If the patient 306 or other equipment is positioned such that a portion of the zone of operation 308 is obscured from view of the navigation camera 340 it may compromise the ability of the navigation system to track tools during surgery. The planning system determines whether the zone of operation 308 is fully visible to the navigation camera within the modelled operating room of the virtual coordinate space, and outputs an alert if full visibility is compromised. For example, if the patient's position and the trajectory of access 302 relative to the navigation camera 340 are such that a portion of the zone of operation 308 is obscured from view due to the patient's skull, as shown in FIG. 4E, then the navigation camera 340 should be repositioned. The planning system may employ a search for ray-tracing collisions within the virtual coordinate space between the navigation camera 340 and points within or defining the zone of operation 308, to determine whether any portion of the zone of operation 308 is blocked from view by the navigation camera 340 by any modelled object in the virtual coordinate space.

In some cases, the line-of-sight evaluation may be partly based upon determining a relative angle between the trajectory of access 302 and the camera line-of-sight. If the trajectory is perpendicular to or at an acute angle to the camera line-of-sight, then the system may determine that the patient's head is unlikely to obscure the view. In some cases, an obtuse angle of up to a predetermined maximum may be permitted.

With a navigation camera 340 having two spaced-apart cameras, the line-of-sight determination may be separately evaluated for each of the two spaced-apart cameras. If either of them is blocked from viewing a part of the zone of operation 308, then an error message or notification may be output by the planning system.

The line-of-sight (e.g. ray tracing) evaluation may be re-performed by the planning system with each change in the operating room layout, including moving any modelled equipment or personnel, or adding models of any new equipment or personnel.

Figure 5:
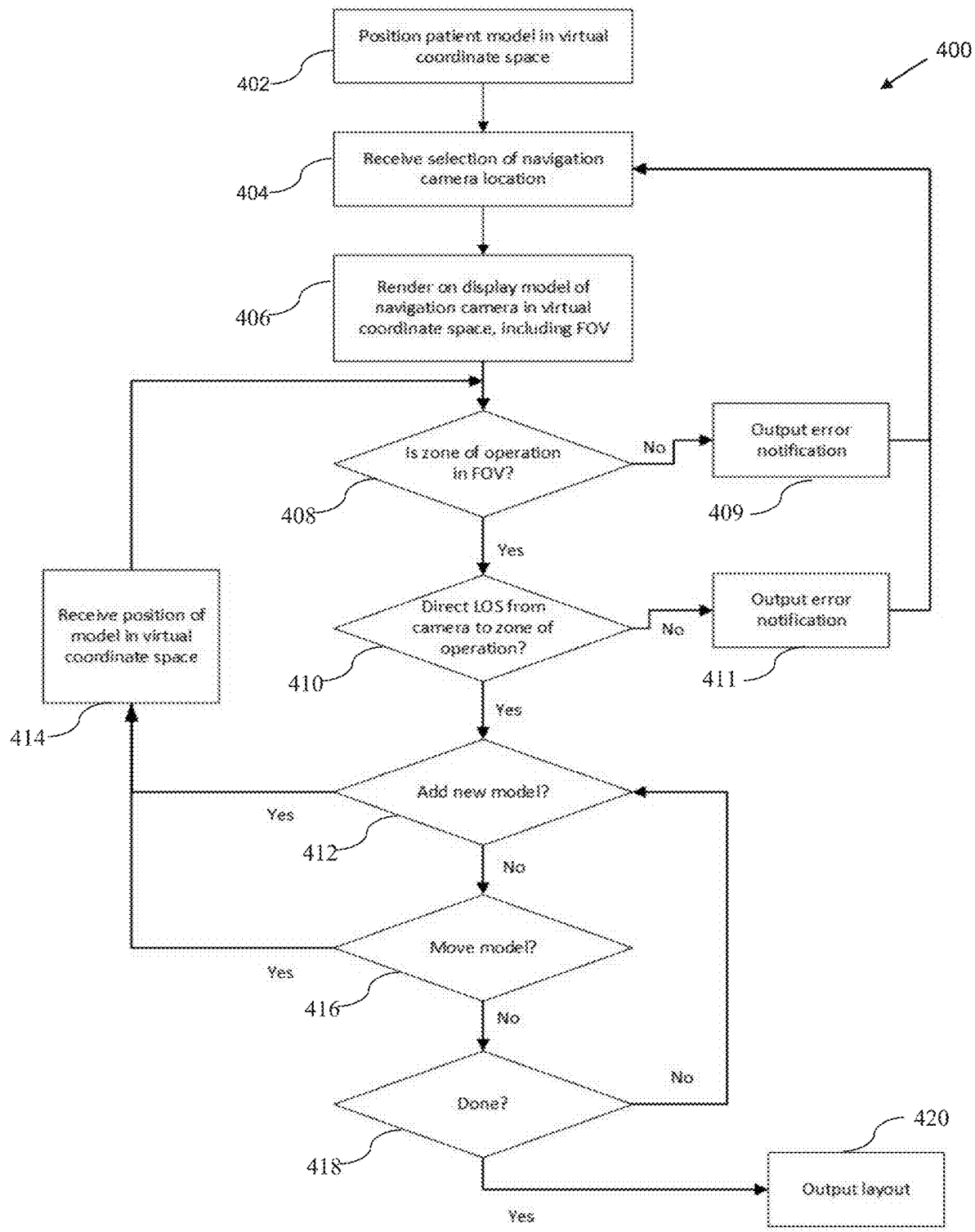
FIG. 5 shows, in flowchart form, one example process for generating an operating room layout plan.

Reference will now be made to FIG. 5, which shows, in flowchart form, an example process 400 for generating an OR layout plan. The process 400 may be implemented on a computing device having at least one processor, a display, memory and processor-executable program instructions that, when executed, cause the at least one processor to carry out the operations of the process 400. The computing device, so configured, may be referred to as a planning system for generating an OR layout plan.

Prior to execution of the process 400 a surgical plan may be developed, including details of a trajectory of access relative to a patient's head or other anatomical features, and the patient's position during surgery given the trajectory of access. The surgical plan, or various details thereof like the trajectory of access, may be uploaded or entered into the planning system. In some embodiments, the planning system may include generating one or more graphical user interface (GUI) display screens to prompt for selection of, or entry of, details of the trajectory of access and/or patient position. Operation 402 of the process 400 includes positioning a patient model in a virtual coordinate system. The patient model is a three-dimension model of the patient (with or without an operating table or associated patient support equipment) that is stored in memory in the system and is positionable in the virtual coordinate system.

The virtual coordinate system defines a plane that indicates the floor of the operating room. It may, in some examples, include perpendicular planes defining the walls of the operating room. In one example, a three-dimensional scan of the actual operating room is uploaded to the planning system and the model of that scanned room is located in the virtual coordinate system.

The patient model is positioned within the virtual coordinate space in operation 402. If the virtual coordinate space includes dimensions of a scanned operating room, it may further include a specified location for the patient in terms of the location of a fixed operating room table, in some examples.

In operation 404, the planning system receives selection of a navigation camera location. This may include user selection of a navigation camera model (e.g. from a menu or list of equipment options), and the indication of the location at which to position the model relative to the patient location. The location of the navigation camera (and any other equipment), may be received as a set of input coordinates (x and y, and possibly z, if the camera has an adjustable height), and an angle of rotation in the x-y plane. In a GUI-based system, the location may be manipulated through the "drag-and-drop" of a model into a rendered view of the virtual coordinate space and subsequent manipulation of the model using one or more input devices (e.g. mouse, keyboard, touchscreen, stylus, etc.).

It will be appreciated that prior to operation 404 models of other equipment and or personnel may be positioned in the virtual coordinate space, but those operations are not illustrated for ease of explanation.

As noted in operation 406, the navigation camera model is positioned in the selected location in the virtual coordinate space and a view of the virtual coordinate space, including the patient and the navigation camera, is rendered on the display. The model of the navigation camera rendered includes visual indication of the field of view of the camera, and visual indication of the zone of operation proximate the patient and encompassing at least a portion of the trajectory of access. The view may be altered through user input, so as to view the virtual coordinate space from a different viewpoint.

The planning system may determine, in operation 408, whether the zone of operation lies within the field of view of the navigation. If not, then in operation 409, the planning system may output an error notification. The error notification may include an auditory alert signaling that the position of the navigation camera is unsuitable, in some cases. In some other cases, the error notification may include a visual alert, such as a warning message and/or coloring of the field of view image, navigation camera model, and/or zone of operation indicator so as to indicate that the position of the navigation camera fails to include the zone of operation. The process 400 then returns to operation 404 to receive an updated location for the navigation camera. It will be appreciated that this example implementation is designed to ensure that the camera is positioned in a location in which the field of view includes the zone of operation before further layout planning is permitted.

In operation 410, the planning system determines whether the camera has a direct line-of-sight to the zone of operation. That is, the system assess whether any other objects modeled in the virtual coordinate space interrupt the direct line-of-sight between the camera and points in the zone of operation. The determination may include testing a field of points within the zone of operation in some examples. The determination may include testing a set of perimeter points at edges of the zone of operation in some examples. Other techniques may be used in other implementations. In some cases, the determination is carried out separately for each of the two or more cameras in the navigation camera. If the line-of-sight is obscured by a modelled object, whether equipment or personnel, an error notification is output. As above, the error notification may be auditory or visual or both. The process 400 may then return to operation 404 to obtain a new location for the navigation camera. In some cases, the planning system may permit adjustment of the location of another object instead of the navigation camera, for example to remove an obstructing object. In some cases, the planning system may permit further planning of the operating room layout, while maintaining the visual indication of the error in positioning of the navigation camera due to an obstructed line of sight. This error may, in some embodiments, prevent the finalization and output of the OR layout plan until corrected.

It will be appreciated that both operations 408 and 410 may be implemented together and performed nearly contemporaneously by the planning system. They are shown separately in the present example flowchart for ease of discussion.

In operation 412, the planning system determines whether addition of a new model to the virtual coordinate space has been requested (e.g. such a request may be received via the GUI display, from a drop-down menu, from a keyboard input, or through other user input). If a new model is to be added, then in operation 414, the system receives location information for the model, positions the model in the virtual coordinate space, and renders the current view including the newly-added model. The process 400 then returns to operation 408 and 410 to assess whether the newly-added item has impacted the suitability of positioning of the navigation camera relative to the zone of operation.

Similarly, in operation 416, the system determines whether movement of one of the existing models has been requested (e.g. through selection of the object in a GUI display using a touchscreen, pointer, mouse or other device). If so, then in operation 414, the system receives new location information for the model, positions the model in the virtual coordinate space, and renders the current view including the moved model. The process 400 then returns to operation 408 and 410 to assess whether the newly-moved object has impacted the suitability of positioning of the navigation camera relative to the zone of operation. The moved object may include the navigation camera itself.

In operation 418, the planning system determines whether the planning has been completed. Certain constraints may be imposed on completion of planning in some embodiments. In one example, output of an OR layout plan may be prohibited until certain required equipment has been included. If output is permitted, then in operation 420 the OR layout plan is output. The plan may be output as (possibly dimensioned) views of the OR, including locations of each of the modeled objects. The output may include a plan view, an elevation view, a perspective view, a rotatable three-dimensional model of the OR, or some or all of these.

In some embodiments, the output in operation 418 includes rendering the OR layout plan within an AR or VR system to enable a viewer to evaluate the layout. In one example, an AR system capable of rendering stereoscopic pseudo-three-dimensional models may be used, such as the Microsoft™ Hololens™ system, for example. In one implementation, the AR system is configured so as to allow a viewer to position him or herself within the OR at the location where the surgeon will be positioned so as to evaluate the OR layout from that position. In some implementations, the modelled equipment may be capable of being actuated; for example, the robotic arm on the drive unit may be moveable (via user input) within its configured range of motion. Accordingly, the surgeon is able to fully evaluate the feasibility and comfort level of the OR layout without having to actually place the equipment in the OR, and adjustments may be easily made to the locations of objects in the OR layout plan if deficiencies are identified without consuming excessive set-up time in the actual OR.

In some embodiments, a staff member or other technician responsible for setting up the operating room according to the OR layout plan may view the room through an AR system that overlays the OR layout plan. The technician may then visually evaluate whether the real world equipment is laid out according to the plan or whether there are deviations. In some embodiments, the AR system may be configured to optically or otherwise detect the location and orientation of the real-world equipment and evaluate correspondence with the modeled equipment to determine whether (a) all equipment is present and (b) the location of the equipment accords with the models within a degree of tolerance.

The OR layout plan may be stored in memory for future use in connection with subsequent surgeries. In some cases, the OR layout plan may be stored in association with a surgeon identifier, since layout specifics may be peculiar to the needs of a particular surgeon. In some cases, the OR layout plan may alternatively or also be stored in association with a surgical procedure identifier since the plan may be specific to a type of surgery.

Figure 6:
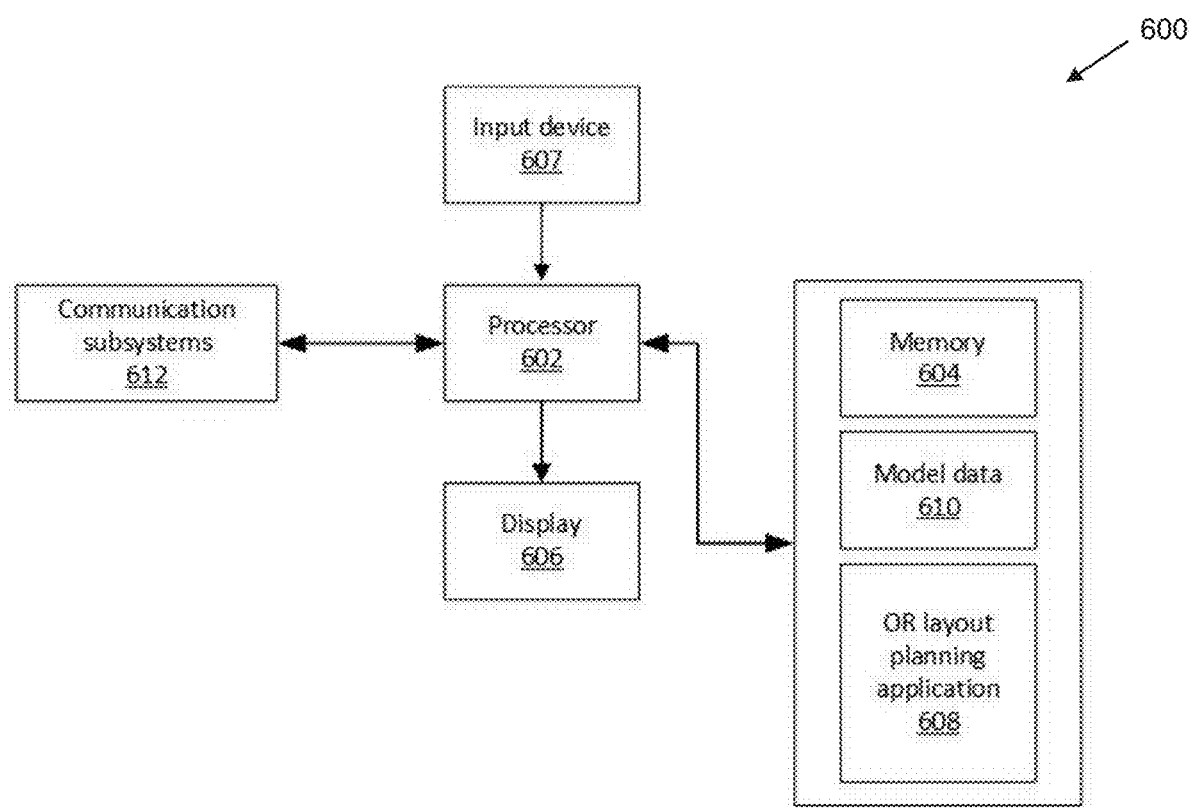
FIG. 6 shows, in block diagram form, an example planning system.

Reference is now made to FIG. 6, which shows an example embodiment of a planning system 600. The planning system 600 includes at least one processor 602 and memory 604. The memory 604 stores an operating room layout planning application 608, containing executable instructions that, when executed by the processor, cause the planning system 600 to carry out operations to enable planning of OR layout, for example as described in connection with the process 400 (FIG. 5). The memory 604 may also store model data 610, describing various three-dimensional models, such as a patient (in various positions), a surgeon, and various surgical equipment and tools that may be placed in the operating room. The planning application 608 causes the processor 602 to define a virtual coordinate space within which one or more of the model may be positioned, and to carry out the described operations of determining whether the navigation camera is positioned suitably vis-à-vis the patient and/or the zone of operation to enable effective tracking of objects during the surgery.

The planning system 600 further includes one or more input devices 607, and includes a display 606 on which the processor may render a view of the virtual coordinate space. In some cases, the planning system 600 may include additional processors, including a graphics processor, to aid in fast rendering of three-dimensional data and carrying out various computations and operations for determining whether modelled objects obstruct a line-of-sight, for example.

In some example embodiments, the planning system 600 include a virtual reality simulator. In such an example, the display 606 may be implemented by way of a headset to be worn by a user, and the view rendered on the screen(s) in the headset may be the view from a defined point in the virtual coordinate space, such as the view from the point-of-view of the surgeon model from its location in the virtual coordinate space. The system thereby permits the surgeon to view the modelled operating room as though in his or her position for surgery to assess suitability of the layout.

The planning system 600 may further include a communication subsystem 612 for receiving data from one or more externals systems, such as, for example pre-operative surgical plan data, or for outputting data regarding the OR layout plan, for example to a printer or to an AR system.

Certain adaptations and modifications of the described embodiments can be made. Therefore, the above discussed embodiments are considered to be illustrative and not restrictive.

What is claimed is:

1. A method of generating, by a computing device, an operating room layout plan for a surgical procedure involving a patient, the method comprising:
   determining a trajectory of access relative to the patient based on a pre-operative surgical plan, the trajectory of access being aligned with an access port for the surgical procedure;
   determining, based in part on the pre-operative surgical plan, one or more possible patient positions, wherein the one or more possible patient positions are limited based on the trajectory of access;
   receiving selection of a patient position selected from the one or more possible patient positions, the selected patient position and the trajectory of access defining a three-dimensional zone of operation within which surgical instruments are tracked by a navigation system, wherein the trajectory of access defines a centerline of the zone of operation;
   defining a patient model at a location in a virtual coordinate space representing the operating room, and rendering the patient model, the trajectory of access and the zone of operation on a display;
   receiving user selection of a navigation camera location in the virtual coordinate space,
      the navigation camera location indicating a location of the navigation camera relative to the patient location in the virtual coordinate space;
   rendering a navigation camera model visually indicating an operative field of view of the navigation camera;
   determining whether the navigation camera has a direct line-of-sight to the zone of operation and, if not, outputting an error indicator; and
   outputting the operating room layout plan based on the location of the patient model and the navigation camera location in the virtual coordinate space.

2. The method claimed in claim 1, further comprising determining whether the operative field of view includes the zone of operation and, if not, outputting an error notification on the display.

3. The method claimed in claim 1, wherein determining whether the navigation camera has a direct line-of-sight to the zone of operation includes receiving selection of a new location for the navigation camera and re-determining whether the navigation camera has a direct line-of-sight to the zone of operation.

4. The method claimed in claim 1, further comprising adding a new model of a new object to the virtual coordinate space and re-determining whether the navigation camera has a direct line-of-sight to the zone of operation.

5. The method claimed in claim 1, further comprising receiving selection of a new location for a model of an object in the virtual coordinate space and re-determining whether the navigation camera has a direct line-of-sight to the zone of operation.

6. The method claimed in claim 1, further comprising:
   receiving a request to add a new model to the virtual coordinate space, wherein the new model includes a range of operation, including a location of the new model, and
   rendering the new model in a view of the virtual coordinate space, including visually indicating the range of operation.

7. The method claimed in claim 6, wherein rendering the new model includes outputting an alert if the range of operation excludes the zone of operation.

8. The method claimed in claim 1, wherein outputting the operating room layout includes rendering the operating room layout plan within an augmented reality system or a virtual reality system.

9. The method claimed in claim 8, further comprising rendering a virtual operating room in the augmented reality system or the virtual reality system from a perspective of a position of a surgeon.

10. The method claimed in claim 8, further comprising detecting, using the augmented reality system, deviations between physical positioning of equipment in the operating room and the operating room layout plan rendered in the augmented reality system.

11. The method claimed in claim 1, wherein outputting includes storing the operating room layout plan in association with a surgeon identifier and a surgical procedure identifier for use in association with a subsequent surgery.

12. An operating room layout planning system for a surgical procedure involving a patient, the system comprising:
   a memory storing a plurality of models and a virtual coordinate space representing the operating room;

a processor coupled to the memory;
a display to render a view of the operating room defined in the virtual coordinate space; and
a planning application containing instructions executable by the processor that, when executed, cause the processor to
determine a trajectory of access relative to the patient based on a pre-operative surgical plan, the trajectory of access being aligned with an access port for the surgical procedure;
determine, based in part on the pre-operative surgical plan, one or more possible patient positions, wherein the one or more possible patient positions are limited based on the trajectory of access;
receive selection of a patient position selected from the one or more possible patient positions, the selected patient position and the trajectory of access defining a zone of operation within which surgical instruments are tracked by a navigation system, wherein the trajectory of access defines a centerline of the zone of operation;
define a patient model at a location in the virtual coordinate space and render the patient model, the trajectory of access and the zone of operation on the display;
receive user selection of a navigation camera location in the virtual coordinate space, the navigation camera location indicating a location of the navigation camera relative to the patient location in the virtual coordinate space;
render a navigation camera model visually indicating an operative field of view of the navigation camera;
determine whether the navigation camera has a direct line-of-sight to the zone of operation and, if not, outputting an error indicator; and
output the operating room layout plan based on the location of the patient model and the navigation camera location in the virtual coordinate space.

13. The system claimed in claim 12, wherein the instructions, when executed, further cause the processor to determine whether the operative field of view includes the zone of operation and, if not, to output an error notification on the display.

14. The system claimed in claim 12, wherein determining whether the camera has a direct line-of-sight to the zone of operation includes receiving selection of a new location for the navigation camera and re-determining whether the navigation camera has a direct line-of-sight to the zone of operation.

15. The system claimed in claim 12, wherein the instructions, when executed, further cause the processor to add a new model of a new object to the virtual coordinate space and re-determine whether the navigation camera has a direct line-of-sight to the zone of operation.

16. The system claimed in claim 12, wherein the instructions, when executed, further cause the processor to receive selection of a new location for a model of an object in the virtual coordinate space and re-determine whether the navigation camera has a direct line-of-sight to the zone of operation.

17. The system claimed in claim 12, wherein the instructions, when executed, further cause the processor to:

receive a request to add a new model to the virtual coordinate space, wherein the new model includes a range of operation, including a location of the new model, and
render the new model in a view of the virtual coordinate space, including visually indicating the range of operation.

18. The system claimed in claim 17, wherein the processor is to render the new model by outputting an alert if the range of operation excludes the zone of operation.

19. The system claimed in claim 12, wherein the processor is to output the operating room layout by rendering the operating room layout plan within an augmented reality system or a virtual reality system.

20. The system claimed in claim 19, further comprising the augmented reality system which is to render the operating room layout plan from a perspective of a position of a surgeon.

21. The system claimed in claim 19, further comprising the augmented reality system which is to detect deviations between physical positioning of equipment in the operating room and the operating room layout plan rendered in the augmented reality system.

22. The system claimed in claim 12, wherein the processor is to output by storing the operating room layout plan in memory in association with a surgeon identifier and a surgical procedure identifier for use in association with a subsequent surgery.

23. A non-transitory computer-readable medium storing processor-executable instructions to generate an operating room layout plan for a surgical procedure involving a patient and a trajectory of access, wherein the instructions, when executed by one or more processors, cause the processors to:
determine a trajectory of access relative to a patient based on a pre-operative surgical plan, the trajectory of access being aligned with an access port for the surgical procedure;
determine, based in part on the pre-operative surgical plan, one or more possible patient positions, wherein the one or more possible patient positions are limited based on the trajectory of access;
receive selection of a patient position selected from the one or more possible patient positions, the selected patient position and the trajectory of access defining a zone of operation within which surgical instruments are tracked by a navigation system, wherein the trajectory of access defines a centerline of the zone of operation;
define a patient model at a location in a virtual coordinate space representing the operating room, and render the patient model, the trajectory of access and the zone of operation on a display;
receive user selection of a navigation camera location in the virtual coordinate space,
the navigation camera location indicating a location of the navigation camera relative to the patient location in the virtual coordinate space;
render a navigation camera model visually indicating an operative field of view of the navigation camera;
determine whether the navigation camera has a direct line-of-sight to the zone of operation and, if not, outputting an error indicator; and
output the operating room layout plan based on the location of the patient model and the navigation camera location in the virtual coordinate space.

* * * * *